United States Patent [19]

Bailly

[11] Patent Number: 5,078,676
[45] Date of Patent: Jan. 7, 1992

[54] CONTROL DEVICE FOR AN ARTIFICIAL SPHINCTER AND IMPLANTABLE PROSTHESIS INCLUDING SAME

[75] Inventor: Pierre Bailly, Montrouge, France

[73] Assignee: SociétéAnonyme dite : SYNTHELABO, Paris, France

[21] Appl. No.: 607,892

[22] Filed: Nov. 1, 1990

[30] Foreign Application Priority Data

Nov. 3, 1989 [FR] France ............................ 89 14402

[51] Int. Cl.⁵ ................................................ A61F 2/48
[52] U.S. Cl. ...................................... 600/31; 623/14; 128/DIG. 25
[58] Field of Search ...................................... 600/29-31; 128/DIG. 25; 623/14; 604/9

[56] References Cited

U.S. PATENT DOCUMENTS

| | | | |
|---|---|---|---|
| 4,056,095 | 11/1977 | Rey et al. | 128/DIG. 25 X |
| 4,222,377 | 9/1980 | Burton | 128/DIG. 25 X |
| 4,417,567 | 11/1983 | Trick | 128/DIG. 25 X |
| 4,419,985 | 12/1983 | Trick | 128/DIG. 25 X |
| 4,437,457 | 3/1984 | Trick et al. | 128/DIG. 25 X |
| 4,571,749 | 2/1986 | Fischell | 623/14 |
| 4,682,583 | 7/1987 | Burton et al. | 128/DIG. 25 X |
| 4,784,660 | 11/1988 | Fischell | 128/DIG. 25 X |
| 4,885,002 | 12/1989 | Watanabe et al. | 604/9 |
| 4,994,020 | 2/1991 | Polyak | 600/31 |

FOREIGN PATENT DOCUMENTS 2614227 10/1976 Fed. Rep. of Germany ... 128/DIG. 25 X

Primary Examiner—Randall L. Green
Assistant Examiner—David H. Willse
Attorney, Agent, or Firm—Marshall, O'Toole, Gerstein, Murray & Bicknell

[57] ABSTRACT

A control device for an artificial sphincter for a natural bodily passage, in particular a urinary passage, which contains a variable volume envelope. The control device includes a first chamber in the form of a balloon, a second chamber defined by two plates joined by a membrane forming a bellows, between which the balloon is accommodated, and an elastic return mechanism including at least one elastic band around the plates.

11 Claims, 3 Drawing Sheets

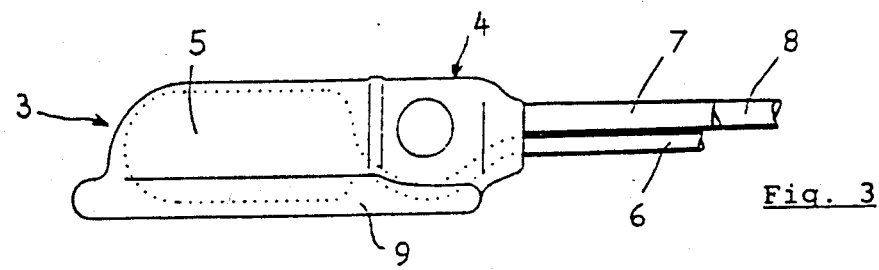
Fig. 3
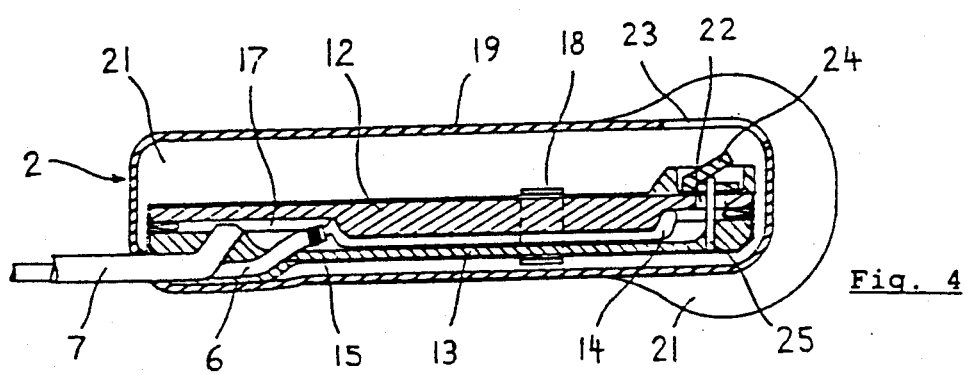
Fig. 4
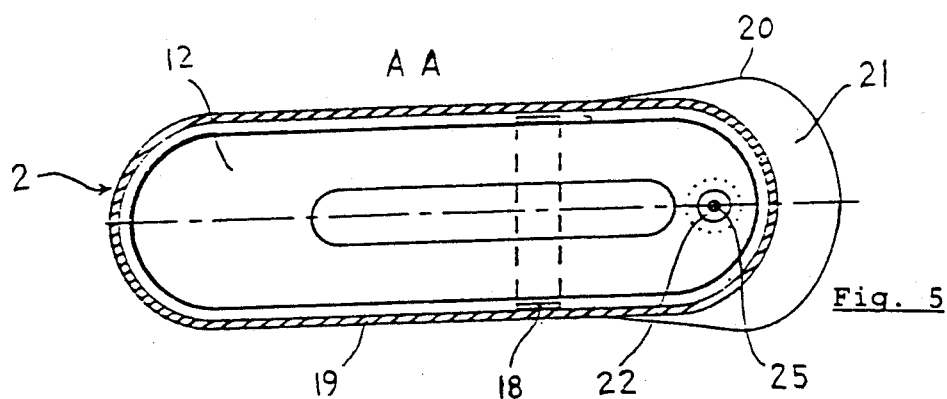
Fig. 5
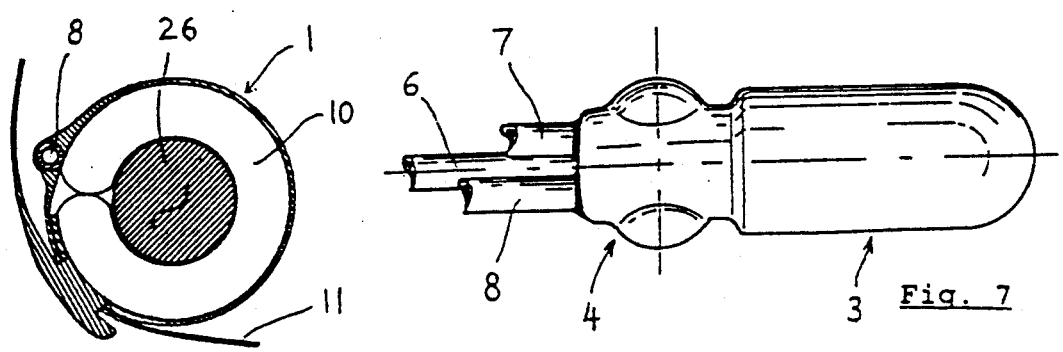
Fig. 6
Fig. 7

CONTROL DEVICE FOR AN ARTIFICIAL SPHINCTER AND IMPLANTABLE PROSTHESIS INCLUDING SAME

BACKGROUND OF THE INVENTION

1. Field of the invention

The present invention concerns a control device for an artificial sphincter for a natural bodily passage, in particular a urinary passage, and an implantable prosthesis comprising said control device.

2. Description of the Prior Art

One known means of remedying the inconveniences of urinary incontinence entails placing around the urethra (in men) or around the vesical cervix (in women) an artificial sphincter in the form of a collar or cuff which selectively compresses the urinary passage as a substitute for the defective natural sphincter.

Devices of this kind are well known and operate satisfactorily. Descriptions of them can be found in U.S. Pat. Nos. 3 863 622, 4 222 377 and U.S. Pat. No. 4 632 114, for example. They comprise, for example, a generally toroidal balloon with a flexible or rigid surround, the assembly being placed around the urinary passage. According to the pressure of the hydraulic fluid inside the balloon, the natural passage is compressed (continence state) or not (urination phase).

Other known artificial sphincter control devices inject a fluid into the cuff to compress the urinary passage or remove fluid from it to release the passage and allow urination. These devices can also be implanted, in the patient's abdomen, for example, and can be operated through the skin.

In the absence of any hardware device passing through the skin, the only simple manipulation that can be performed through the skin is to exert pressure on an implanted control device, by pressing with a finger, for example. Also, the continence state is the usual state, with the result that the artificial sphincter must remain pressurized for long periods, being released only during urination.

There is already known from U.S. Pat. No. 4 571 749 an implantable urinary sphincter system in which the control device comprises a bellows connected to a vessel filled with incompressible fluid comprising a flexible membrane. When the patient presses hard with the fingers on said membrane the length of the bellows is increased which in turn increases the volume of a chamber filled with incompressible fluid connected to the sphincter, so reducing the pressure in said sphincter. On the other hand, when no pressure is exerted on the membrane, the return force exerted by a diaphragm constituting one wall of said chamber tends to return the latter to its original volume, so as to compress the sphincter.

This device has a number of disadvantages, however. Firstly, the action of the patient on the membrane may not result in sufficient lengthening of the bellows because of the shape of the membrane or because the vessel may expand rather than the bellows. What is more, the end surface of the bellows, acting on the corresponding wall of the chamber connected to the sphincter, is small, which does not guarantee effective action of said bellows on said chamber. Also, the structure of the control device described in U.S. Pat. No. 4 571 749 is complex and therefore costly and unreliable.

An object of the present invention is to avoid these disadvantages and the invention consists in an artificial sphincter control device of simple, reliable and economical construction.

SUMMARY OF THE INVENTION

In one aspect, the present invention consists in a control device for an artificial sphincter for a natural bodily passage, in particular a urinary passage, said sphincter comprising a variable volume envelope, said device comprising a first chamber containing an incompressible fluid in communication with an actuator device enabling the volume of said first chamber to be varied, a second chamber containing an incompressible fluid in communication with said sphincter, said first and second chambers being so adapted that a variation in the volume of said first chamber causes a variation in the same direction of the volume of said second chamber, said device being adapted, by actuation of said actuator device, to change from a first state in which the volumes of said first and second chambers are minimal, the sphincter then closing said natural passage, to a second state in which the volumes of said first and second chambers are maximal, the sphincter then opening said passage, elastic return means being provided to return said device from said second state to said first state, in which device said first chamber is a balloon, said second chamber is defined by two plates joined by a membrane forming a bellows between which said balloon is accommodated, and said elastic return means comprise at least one elastic band around said plates.

The fact that the first chamber is in the form of a balloon which reacts to any patient action on the actuator member and the fact that said balloon is accommodated between the two plates of the second chamber, with which it is in close contact over a large part of its surface, guarantee that the control device in accordance with the invention is totally effective. In particular, a specific increase in the volume of the balloon results directly in a corresponding increase in the volume of the second chamber.

Advantageously, said first and second chambers are accommodated in a rigid or semi-rigid casing communicating with a reservoir balloon through an orifice formed in the wall of the casing and so defining a third chamber and there are provided between said second and third chambers fluid connection means whereby communication can be established between said second and third chambers when said plates are relatively close together and said second and third chambers can be isolated from each other when said plates are relatively far apart.

In particular, said fluid connection means between said second and third chambers comprise an orifice formed in one of said plates adapted to be opened or closed by a mobile valve which closes the passage when said plates are relatively far apart and which opens said passage, by abutting on a rod fixed to the other of said plates, when said plates are relatively close together.

Preferably, said plates have their surfaces facing towards each other configured in order to locate the balloon.

In particular, if the balloon is substantially cylindrical when inflated, one of said plates incorporates a part-circular cross-section cavity and the other plate comprises a convex portion conjugate to said cavity, to locate said balloon.

Advantageously, said actuator device comprises a flexible incompressible fluid reservoir.

Also, the control device may comprise a blocking member adapted to interrupt temporarily fluid communication between said sphincter and second chamber, said blocking member advantageously comprises an elastic material body incorporating two substantially spherical chambers communicating with each other and a ball adapted to be housed in one or the other of said chambers, and said body is preferably fixed to said actuator device.

In another aspect, the invention consists in an implantable prosthesis including an artificial sphincter for a natural bodily passage, in particular a urinary passage, said sphincter having a variable volume envelope, and a control device comprising a first chamber containing an incompressible fluid in communication with an actuator device enabling the volume of said first chamber to be varied, a second chamber containing an incompressible fluid in communication with said sphincter, said first and second chambers being so adapted that a variation in the volume of said first chamber causes a variation in the same direction of the volume of said second chamber, said device being adapted, by actuation of said actuator device, to change from a first state in which the volumes of said first and second chambers are minimal, the sphincter then closing said natural passage, to a second state in which the volumes of said first and second chambers are maximal, the sphincter then opening said passage, elastic return means being provided to return said device from said second state to said first state, in which prosthesis said first chamber is a balloon, said second chamber is defined by two plates joined by a membrane forming a bellows between which said balloon is accommodated, said elastic return means comprise at least one elastic band around said plates, and said second chamber is connected by a fluid connection to said sphincter.

The appended drawings will assist a better understanding of the theory and of one embodiment of the invention.

BRIEF DESCRIPTION OF THE DRAWINGS

FIGS. 3 through 12 show in detail one embodiment of a prosthesis of this kind and in particular the control device.

DETAILED DESCRIPTION OF THE INVENTION

Figure 1:
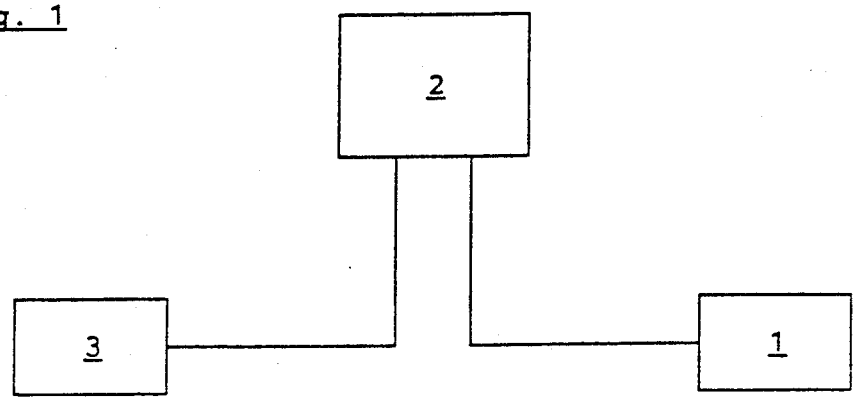
FIGS. 1 and 2 illustrate the operating principle of a prosthesis comprising an artificial sphincter and a control device.

Referring to FIG. 1, a prosthesis comprises an artificial sphincter or cuff 1 connected by a tube to a control device 2 connected by a tube to an actuator device 3.

Figure 2:
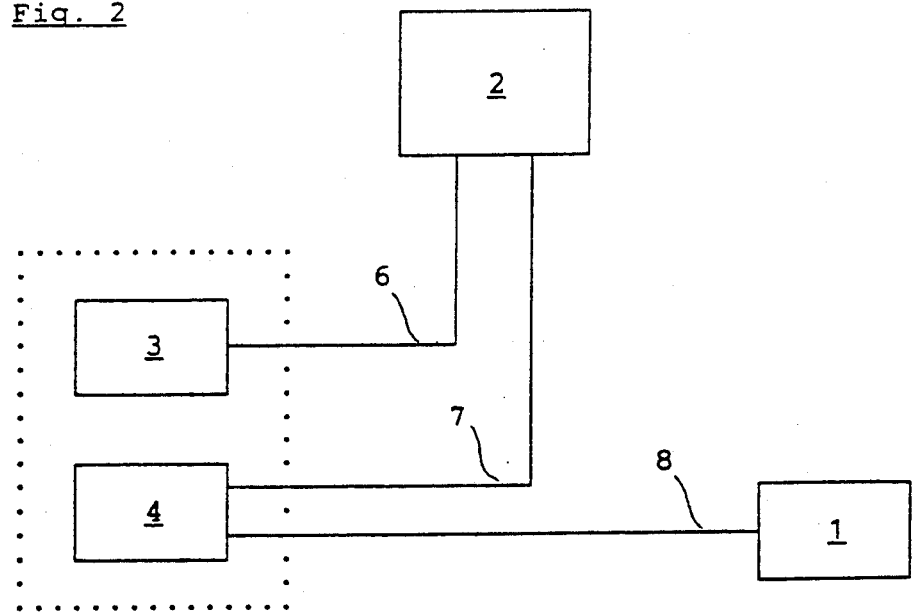

FIG. 2 shows a prosthesis comprising between the control device 2 and the cuff 1 a device 4 for preventing circulation of fluid. The device 4 operates on an "on or off" basis, like a switch or circuit-breaker. It means that the cuff 1 can remain in a permanent state, irrespective of the action exerted on the actuator device 3. In particular, it means that the cuff can be left permanently depressurized, after pressing on the actuator device, so that the patient remains incontinent, for example during the period of healing after fitting the prosthesis or during endoscopic examination.

Like the actuator device 3, the blocking device 4 can be implanted and manipulated through the skin. For convenience, particularly during implantation of the prosthesis, it may be attached to the actuator device 3, as symbolically represented by the dotted rectangle in FIG. 2.

The prosthesis as a whole therefore comprises three components, namely the cuff 1, the control device 2 and the actuator and blocking device 3/4. The three components are interconnected by flexible tubes 6, 7 and 8, as shown in FIG. 2.

Figure 8:
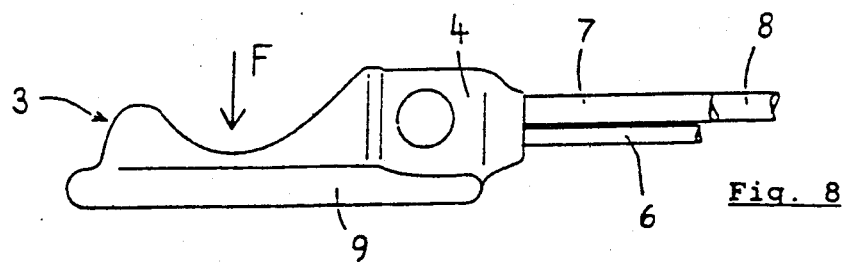

FIGS. 3, 7 and 8 show one embodiment of the actuator and blocking device 3/4.

The actuator device 3 essentially comprises a flexible material chamber or reservoir 5 connected to the control device 2 by a flexible tube 6. A force F applied to the chamber 5 crushes it (FIG. 8) so that some of the fluid it contains is expelled through the tube 6. Removing the force F enables a return to the initial state.

The blocking device 4 comprises an elastic material body containing two spherical chambers intersecting one another, one of which contains a ball. According to whether the ball is in one or other of the spherical chambers, hydraulic fluid can or cannot flow between the inlet/outlet tubes 7/8 of the blocking device 4. Said ball can be passed from one chamber to the other by manipulating the blocking device through the skin.

A hydraulic blocking device as used in the present invention is described in detail in French patent application No 89 06244.

As explained previously, the blocking device 4 and the actuator device 3 preferably constitute a single functional unit. FIGS. 3 and 8 show that the latter can advantageously be provided with a baseplate or base 9 which has a substantially planar surface which can be located against a sufficiently firm support for the force F exerted on the actuator device 3 to deform the chamber 5 effectively without the assembly 3/4 moving.

FIG. 7 shows an alternative functional unit 3/4 with no base 9.

Figure 11:
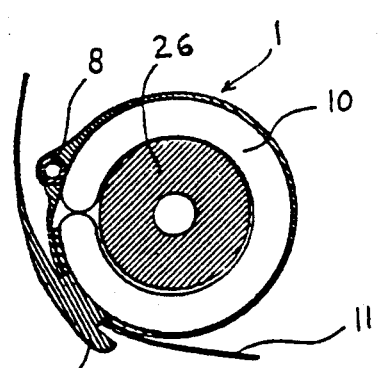

FIGS. 6 and 11 show in cross-section a cuff 1 which can be used for the purposes of the invention. This cuff comprises a flexible tube 8 (seen in transverse cross-section in FIGS. 6 and 11) communicating with the interior of a toroidal balloon 10 and either directly with a control device as shown in FIG. 1 or, preferably, with the blocking device 4 as shown in figure 2. The balloon 10 is preferably pre-formed to avoid the formation of creases when it is inflated and is surrounded by an inextensible strap 11 closed by a known type of button or rack system.

FIG. 6 shows the cuff in the state in which it secures continence, that is to say with the balloon 10 inflated and the urinary passage 26 compressed. FIG. 11 shows the cuff in the state in which it secures incontinence and allows urination, that is to say with the balloon 10 deflated and the urinary passage 26 not compressed.

Figure 9:
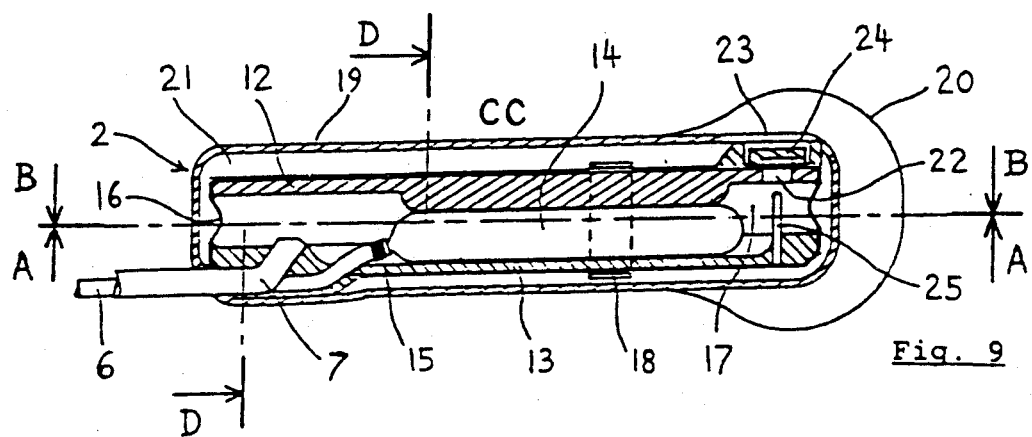
Figure 10:
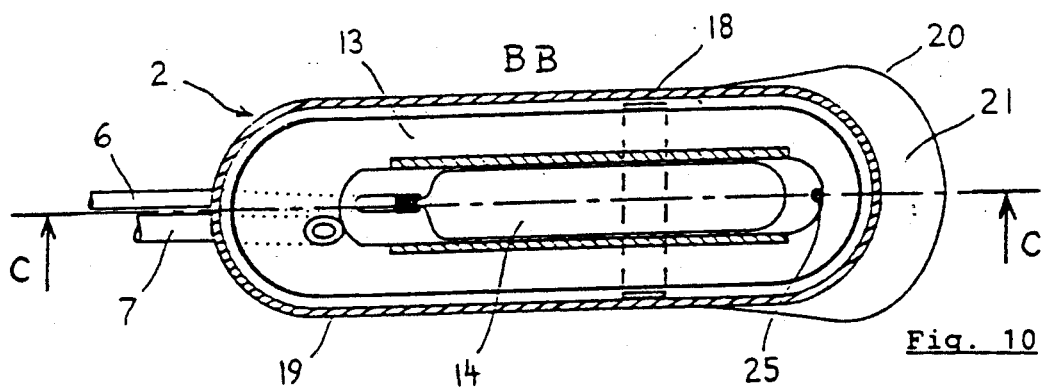
Figure 12:
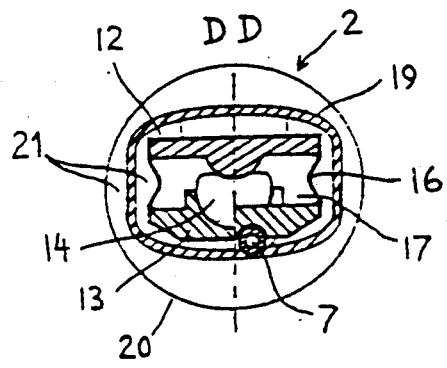

FIGS. 4, 5, 9, 10 and 12 show the control device 2 in cross-section. FIGS. 4 and 5 show it in the continence state and FIGS. 9, 10 and 12 show it during the urination phase.

The control device according to the invention comprises a rigid top plate 12 and a rigid bottom plate 13 between which is disposed a balloon 14 filled with incompressible fluid and communicating with the actuator device 3 through a flexible tube 6 by means of a connection 15 such as a ligature, said tube 6 passing through the bottom plate 13.

Seen face on (FIGS. 5 and 10), both plates 12 and 13 are the same shape, for example oval or rectangular with rounded corners. They face each other and are surrounded by a flexible membrane 16 forming a bellows. This membrane can be adhesively bonded to the edges of the plates 12 and 13 but, to obtain a better seal, it preferably envelops completely both plates and has apertures in it only facing the corresponding orifices in the plates.

The two plates 12 and 13 and the bellows 16 delimit a chamber 17 partly occupied by the balloon 14. The chamber 17 is filled with hydraulic fluid and communicates either directly with the cuff (FIG. 1) or with the blocking device 4 (FIG. 2) through a flexible tube 7 which also passes through the bottom plate 13.

An elastic band 18 runs around the assembly comprising the two plates 12 and 13 and the bellows 16 and urges said plates towards each other so as to reduce the volume of the chamber 17 and to crush the balloon 14. When hydraulic fluid is injected into the balloon 14 the latter inflates and urges the two plates 12 and 13 apart to increase the volume of the chamber 17.

The assembly comprising the two plates 12 and 13 and the bellows 16 containing the balloon 14 and surrounded by the band 18 is itself contained in a rigid or semi-rigid sealed casing 19 through which the tubes 6 and 7 pass and whose interior communicates at all times with a reservoir balloon 20 through an orifice 23 formed in the wall of the casing 19. The balloon partially surrounds the casing 19 and together they delimit a chamber 21 which is also filled with hydraulic fluid and which can be put into communication with the chamber 17.

To this end the chamber 17 is provided with opening and closing means discharging into the chamber 21 and whose state depends on the relative position of the two plates 12 and 13. The function of the opening and closing means is to put the chambers 17 and 21 in communication when the two plates 12 and 13 are relatively close together and to isolate them from each other when the two plates are pushed relatively far apart by the inflation of the balloon 18.

Thus in one specific embodiment the top plate 12 is pierced by an orifice 22 which can be opened or closed by a mobile valve 24. When the two plates 12 and 13 are moved apart the valve 24 closes the orifice 22. When the balloon 14 is emptied and the two plates move towards each other due to the action of the band 18 the valve 24 opens the orifice when it abuts on a rod 25 attached to the bottom plate 13 which moves it away from its closed position. As a result, hydraulic fluid can flow between the chambers 17 and 21 and the pressures in them are equalized.

When the balloon 14 is inflated and pushes the plates 12 and 13 apart the valve 24 disengages from the rod 25 and resumes its closed position and a seal is provided between the chambers 17 and 21 by virtue of the reduced pressure created in the chamber 17, the valve 24 being then applied more firmly to the communication orifice 22.

In theory, both the plates 12 and 13 can have plane surfaces. However, and as shown in FIGS. 4, 5, 9, 10 and 12, the two surfaces of the plates facing each other can advantageously have shapes adapted to locate the balloon 14 correctly. Thus one of the plates, the bottom plate 13, for example, may comprise a cavity or recess adapted to the shape of the balloon 14, for example part-circular if the balloon is substantially cylindrical when inflated. To guarantee effective crushing of the balloon 14 by the top plate 12 the latter may have a convex shape conjugate with that of the cavity in the bottom plate 13.

How the prosthesis in accordance with the invention works and how it is operated are evident from the foregoing description. These aspects are summarized and expanded in the following explanations. It will be assumed that the prosthesis has been implanted in a patient, that is to say that the cuff 1 surrounds the urethra or the vesical cervix, that the functional unit 3, 4 is accessible to the patient and that the control device 2 has been implanted in the abdomen, the three components being interconnected by flexible tubes as shown in FIG. 2.

In the rest position, that is to say in the continence state (FIGS. 3 through 6), no force F is exerted on the actuator device 3, the balloon 14 is deflated, the plates 12 and 13 are pressed together by the band 18, the chamber 17 has its minimal volume and, through the intermediary of the tube 7, the blocking device 4 (in the open condition) and the tube 8, the balloon 10 of the cuff 1 has its maximal volume and therefore compresses the urinary passage 26. The valve 24 is then in the open position, the chambers 17 and 21 communicating with each other, and the pressure in these chambers is the same as that in the balloon 10 of the cuff 1.

By virtue of the flexibility of the reservoir balloon 20, any variation in pressure in the abdomen of the patient is immediately transmitted to the chamber 20 and therefore to the chamber 17 and to the balloon 10 of the cuff 1.

Thus if the abdominal wall of the patient is contracted, for example due to muscular effort, coughing, laughing, hiccups, etc, the increase in pressure on the bladder (which tends to cause urine to leak) also increases the compression of the urinary passage, so that continence is preserved.

In the urination phase (FIGS. 8 through 12), a force F is applied to the actuator device 3 and hydraulic fluid is expelled from it through the tube 6 to fill the balloon 14 of the control device 2. Said balloon 14 acts like a jack to move apart the plates 12 and 13, the orifice 22 is closed by the valve 24 and, because of the increase in the volume of the chamber 17, which is no longer in communication with the chamber 21, the pressure is reduced in the chamber 17 which tends to aspirate hydraulic fluid from the balloon 10 of the cuff 1 through the tube 8, the blocking device 4 (in the open condition) and the tube 7. As the balloon 10 is no longer pressurized, the urinary passage is no longer compressed and urination is made possible.

At the end of this operation the return to the rest state is effected as already described: removal of the force F, return of fluid from the balloon 14 to the actuator device 3, movement of the plates 12 and 13 towards each other, decrease in the volume of the chamber 17, which is again placed in communication with the chamber 21, and increase in the volume of the balloon 10 of the cuff 1, which compresses the urinary passage 26.

Finally, as already mentioned, the presence of a blocking device 4 makes it possible to maintain the patient in a state of incontinence: after application of the force F, it is sufficient to put the blocking device 4 into the off condition to prevent hydraulic fluid returning to the balloon 10.

The materials from which the control device in accordance with the invention is made will be evident to those skilled in the art, given the mechanical and physiological properties required of each component part, and given their method of manufacture, which is essentially by molding. The balloon 14 is made from a flexible, non-elastic material such as polyethylene, for example; the plates 12 and 13 and the abutment rod 25 are made from a rigid material such as ethylene polyterephtalate, for example; the valve 24 is made from a semi-rigid material such as silicone rubber, for example; the elastic band 18 is made from an elastic material such as silicone rubber, for example; the bellows 16 is made from a flexible and elastic material such as silicone rubber, for example; the casing 19 is made from a rigid or semi-rigid material and the reservoir balloon 20 is made from a flexible and elastic material and, being welded together, they are both made from silicone rubber, for example; the tubes 6 and 7 are made from a flexible and non-elastic material such as silicone rubber, for example.

It is evident that the generic term "silicone rubber" used here designates only the chemical nature of a material and that it means both rigid materials and flexible or elastic materials, from which those skilled in the art will know how to make an appropriate choice.

The dimensions of the control device are determined according to the volume of hydraulic fluid to be injected into or removed from the cuff 1 to inflate or deflate the balloon 10. For example, if the volume of fluid exchanged is in the order of 1 ml, the overall length of the control device may be 60 to 80 mm, the other dimensions being then proportional to this as suggested by the appended drawings.

Finally, the hydraulic fluid employed in the control device and in the prosthesis as a whole must obviously be a physiologically acceptable liquid which is iso-osmotic inside the body, such as physiological saline, for example.

There is claimed:

1. Control device for an artificial sphincter for a natural bodily passage, said sphincter comprising a variable volume envelope, said device comprising a first chamber containing an incompressible fluid in communication with an actuator device enabling the volume of said first chamber to be varied, a second chamber containing an incompressible fluid n communication with said sphincter, said first and second chambers being so adapted that a variation in the volume of said first chamber causes a variation in the same direction of the volume of said second chamber, said device being adapted, by actuation of said actuator device, to change from a first state in which the volumes of said first and second chambers are minimal, the sphincter then closing said natural passage, to a second state in which the volumes of said first and second chambers are maximal, the sphincter then opening said passage, elastic return means being provided to return said device from said second state to said first state, in which device said first chamber is a balloon, said second chamber is defined by two plates joined by a membrane forming a bellows between which said balloon is accommodated, and said elastic return means comprises at least one elastic band around said plates, said first and second chambers being accommodated in a rigid or semi-rigid casing communicating with a reservoir balloon through an orifice formed in the wall of the casing and so defining a third chamber and there are provided between said second and third chambers fluid connection means whereby communication can be established between said second and third chambers when said plates are relatively close together and said second and third chambers can be isolated from each other when said plates are relatively far apart.

2. Device according to claim 1 wherein said artificial sphincter is adapted for a urinary passage.

3. Device according to claim 1 wherein said fluid connection means between said second and third chambers comprise an orifice formed in one of said plates adapted to be opened or closed by a mobile valve which closes the passage when said plates are relatively far apart and which opens said passage, by abutting on a rod fixed to the other of said plates, when said plates are relatively close together.

4. Device according to claim 1 wherein said plates have their surfaces facing towards each other configured in order to locate the balloon.

5. Device according to claim 4 wherein the balloon is substantially cylindrical when inflated, one of said plates incorporates a part-circular cross-section cavity and the other plate comprises a convex portion conjugate to said cavity, to locate said balloon.

6. Device according to claim 1 wherein said actuator device comprises a flexible incompressible fluid reservoir.

7. Device according to claim 1 comprising a blocking member adapted to interrupt temporarily fluid communication between said sphincter and second chamber.

8. Device according to claim 7 wherein said blocking member comprises an elastic material body incorporating two substantially spherical chambers communicating with each other and a ball adapted to be housed in one or the other of said chambers.

9. Device according to claim 8 wherein said body is fixed to said actuator device.

10. Implantable prosthesis including an artificial sphincter for a natural bodily passage, said sphincter having a variable volume envelope, and a control device comprising a first chamber containing an incompressible fluid in communication with an actuator device enabling the volume of said first chamber to be varied, a second chamber containing an incompressible fluid in communication with said sphincter, said first and second chambers being so adapted that a variation in the volume of said first chamber causes a variation in the same direction of the volume of said second chamber, said device being adapted, by actuation of said actuator device, to change from a first state in which the volumes of said first and second chambers are minimal, the sphincter then closing said natural passage, to a second state in which the volumes of said first and second chambers are maximal, the sphincter then opening said passage, elastic return means being provided to return said device from said second state to said first state, in which prosthesis said first chamber is a balloon, said second chamber is defined by two plates joined by a membrane forming a bellows between which said balloon is accommodated, said elastic return means comprise at least one elastic band around said plates, said first and second chambers being accommodated in a rigid or semi-rigid casing communicating with a reservoir balloon through an orifice formed in the wall of the casing and so defining a third chamber and there are provided between said second and third chambers fluid connection means whereby communication can be established between said second and third chambers when said plates are relatively close together and said second and third chambers can be isolated from each other when said plates are relatively far apart.

11. Prosthesis according to claim 10 wherein said artificial sphincter is adapted for a urinary passage.

* * * * *